US010240201B2

(12) United States Patent
Takahashi et al.

(10) Patent No.: US 10,240,201 B2
(45) Date of Patent: Mar. 26, 2019

(54) EYE DISEASE TREATMENT AGENT, SCREENING METHOD THEREFOR, AND METHOD FOR PREDICTING REJECTION RESPONSE ASSOCIATED WITH RETINAL PIGMENT EPITHELIAL CELL TRANSPLANT

(71) Applicant: Healios K.K., Tokyo (JP)

(72) Inventors: Masayo Takahashi, Saitama (JP); Sunao Sugita, Saitama (JP)

(73) Assignee: Healios K.K., Tokyo (JP)

( * ) Notice: Subject to any disclaimer, the term of this patent is extended or adjusted under 35 U.S.C. 154(b) by 79 days.

(21) Appl. No.: 15/120,433

(22) PCT Filed: Feb. 20, 2015

(86) PCT No.: PCT/JP2015/054871
§ 371 (c)(1),
(2) Date: Aug. 19, 2016

(87) PCT Pub. No.: WO2015/125941
PCT Pub. Date: Aug. 27, 2015

(65) Prior Publication Data
US 2017/0009298 A1    Jan. 12, 2017

(30) Foreign Application Priority Data
Feb. 21, 2014 (JP) ................................ 2014-032325

(51) Int. Cl.
| C12Q 1/6883 | (2018.01) |
| A61K 35/30 | (2015.01) |
| G01N 33/68 | (2006.01) |
| A61L 27/36 | (2006.01) |

(52) U.S. Cl.
CPC ............ *C12Q 1/6883* (2013.01); *A61K 35/30* (2013.01); *A61L 27/3604* (2013.01); *A61L 27/3666* (2013.01); *G01N 33/6863* (2013.01); *G01N 33/6866* (2013.01); *G01N 33/6893* (2013.01); *A61L 2430/16* (2013.01); *C12Q 2600/136* (2013.01); *C12Q 2600/156* (2013.01); *G01N 2333/57* (2013.01); *G01N 2333/96433* (2013.01); *G01N 2500/10* (2013.01); *G01N 2800/245* (2013.01)

(58) Field of Classification Search
None
See application file for complete search history.

(56) References Cited

U.S. PATENT DOCUMENTS

| 2006/0031951 A1 | 2/2006 | Klimanskaya |
| 2008/0299091 A1 | 12/2008 | Revazova et al. |
| 2011/0165130 A1 | 7/2011 | Guenou |
| 2013/0149284 A1 | 6/2013 | Malcuit et al. |
| 2014/0057281 A1 | 2/2014 | Takahashi et al. |
| 2015/0250828 A1 | 9/2015 | Kamao et al. |

FOREIGN PATENT DOCUMENTS

| JP | 2008-530984 A | 8/2008 | |
| JP | 2010-525794 A | 7/2010 | |
| JP | 2011-525370 A | 9/2011 | |
| WO | 2011/063005 A2 | 5/2011 | |
| WO | WO-2011063005 A2 * | 5/2011 | ............. A61K 35/12 |
| WO | 2012/115244 A1 | 8/2012 | |
| WO | 2014/030749 A1 | 2/2014 | |

OTHER PUBLICATIONS

Reinhard et al., "Improvement of graft prognosis in penetrating normal-risk keratoplasty by", Eye, vol. 18, pp. 269-277. (Year: 2004).*
Koretzky, "Multiple Roles of CD4 and CD8 in T Cell Activation", Journal of Immunology, vol. 185, pp. 2643-2644. (Year: 2010).*
Sugita, "Retinal regeneration with iPS cells—Clinical trials for retinal degenerative disorders", Japanese Journal of Clinical Immunology 2015, vol. 38, No. 2, pp. 79-85.
Bartels et al., "Influence of HLA-A, HLA-B, and HLA-DR matching on rejection of random corneal grafts using corneal tissue for retrospective DNA HLA typing", The British Journal of Opthalmology, Nov. 2001, vol. 85, No. 11, pp. 1341-1346.
Klimanskaya et al., "Derivation and Comparative Assessment of Retinal Pigment Epithelium from Human Embryonic Stem Cells Using Transcriptomics", Cloning and Stem Cells, Mary Ann Liebert, Inc. vol. 6, No. 3, 2004, pp. 217-245.
Kamao et al., "Characterization of Human Induced Pluripotent Stem Cell-Derived Retinal Pigment Epithelium Cell Sheets Aiming for Clinical Application", Stem Cell Reports, vol. 2, No. 2, Feb. 1, 2014, pp. 205-218.
Yaji et al., "Transplantation of tissue-engineered retinal pigment epithelial cell sheets in a rabbit model", Biomaterials, Elsevier Science Publishers, vol. 30, No. 5, Feb. 1, 2009, pp. 797-803.
Völker-Dieben, et al., "Beneficial Effect of HLA-DR Matching on the Survival of Corneal Allografts1", Transplantation, vol. 70, No. 4, Aug. 1, 2000, pp. 640-648.
Supplementary Partial European Search Report, dated Sep. 18, 2017 in corresponding European Application No. EP 15 75 1431.
S. Sugita et al., "CTLA-4+ CD8+ T Cells That Encounter B7-2+ Iris Pigment Epithelial Cells Express Their Own B7-2 to Achieve Global Suppression of T Cell Activation", The Journal of Immunology, vol. 172, pp. 4184-4194 (2004).
S. Sugita et al., "B7+ Iris Pigment Epithelium Induce CD8+ T Regulatory Cells; Both Suppress CTLA-4+ T Cells", The Journal of Immunology, vol. 176, pp. 118-127 (2006).
S. Sugita et al., "Retinal Pigment Epithelium-Derived CTLA-2 a Induces TGFb-Producing T Regulatory Cells", The Journal of Immunology, vol. 181, pp. 7525-7536 (2008).

(Continued)

*Primary Examiner* — Michelle F. Paguio Frising
(74) *Attorney, Agent, or Firm* — Mintz Levin Cohn Ferris Glovsky and Popeo, P.C.

(57) ABSTRACT

The present invention provides an agent for treating ophthalmic diseases and a screening method for an agent for treating ophthalmic diseases and the like. The present invention also provides a method for predicting rejection associated with transplantation of retinal pigment epithelial cell to patients with ophthalmic diseases.

2 Claims, 11 Drawing Sheets

(56) References Cited

OTHER PUBLICATIONS

S. Sugita et al., "Acquisition of T Regulatory Functionin Cathepsin L-Inhibited T Cells by Eye-Derived CTLA-2a during Inflammatory Conditions", The Journal of Immunology, vol. 183, pp. 5013-5022 (2009).

S. Sugita et al., "Suppression of IL-22-Producing T Helper 22 Cells by RPE Cells via PD-L1/PD-1 Interactions", IOVS, 54(10), pp. 6926-6933 (2013).

V. Enzmann et al., "Molecular and cellular evidence for T-cell stimulation by allogeneic retinal pigment epithelium cells in vitro", Graefe's Arch Clin Exp Ophthalmol, vol. 239, pp. 445-451 (2001).

V. Enzmann et al., "Effective chemokines and cytokines in the rejection of human retinal pigment epithelium (RPE) cells grafts", Transplant Immunology, vol. 7, pp. 9-14 (1999).

International Search Report in corresponding PCT application No. PCT/JP2015/054871, dated May 19, 2015.

International Search Report issued in corresponding International Application No. PCT/JP2015/054871, May 19, 2015, 4 pages.

* cited by examiner

*P < 0.05、**P < 0.005、n.s. – not significant

|  | IL-2 | IFN-γ | IL-17 | TNF-α | IL-22 |
|---|---|---|---|---|---|
| T cell alone | 0 % | 23 % | 13 % | 21 % | 3 % |
| Tcells+iPS-RPE | 0 % | 27 % | 18 % | 23 % | 3 % |

|  | Granzyme B | Perforin | TNF-α |
|---|---|---|---|
| T cell alone | 22 % | 24 % | 11 % |
| Tcells+iPS-RPE | 27 % | 27 % | 14 % |

EYE DISEASE TREATMENT AGENT, SCREENING METHOD THEREFOR, AND METHOD FOR PREDICTING REJECTION RESPONSE ASSOCIATED WITH RETINAL PIGMENT EPITHELIAL CELL TRANSPLANT

CROSS REFERENCE TO RELATED APPLICATIONS

This application is the U.S. national stage pursuant to 35 U.S.C. § 371, of Japanese International Application Ser. No. PCT/JP2015/054871, filed Feb. 20, 2015 and published in Japanese on Aug. 27, 2015 as publication WO2015/125941 A1, which claims the benefit of Japanese Patent Application Serial No. 2014-032325, filed Feb. 21, 2014, the entire contents of which are hereby incorporated by reference in their entirety.

TECHNICAL FIELD

The present invention relates to an agent for treating ophthalmic diseases, a screening method therefor and a method for predicting a rejection response associated with retinal pigment epithelial cell transplantation.

BACKGROUND ART

Major histocompatibility complex (MHC) is known as HLA (human leukocyte antigen) in human and is expressed in almost all cells and tissues. HLA mainly contains 6 gene loci antigens of A, B, C, DR, DQ and DP, each of which is constituted of complicated combinations of several dozen kinds of different types (allele) in tens of thousands of combinations. HLA is responsible for an important immune mechanism in the human body and the main role thereof is presentation of antigen to recognize self or non-self. When a person receives transplantation of a cell or tissue derived from other person (allogeneic transplantation), HLA is recognized as the most important antigen (foreign substance) by immunocompetent cells such as T cells and the like, whereby rejection is formed and the transplant is not engrafted.

In normal organ transplantation, particularly bone marrow transplantation, it is considered that all 6 gene loci of respective antigens A, B, C, DR, DQ and DP of HLA should in principle match; when they do not match, a risk of severe rejection response and bad prognosis after transplantation are foreseeable.

It is known that retinal pigment epithelial cell expresses or produces a molecule suppressing inflammatory cells that infiltrate intraocularly (Th1 cell, CD8 positive cell, macrophage, B cell and the like), and affords a suppressive signal on allogeneic autologous inflammatory cells (e.g., non-patent documents 1, 2). On the other hand, it is known that retinal pigment epithelial cell affords a promotive signal on regulatory T cells under similar conditions (non-patent documents 3, 4). On the other hand, retinal pigment epithelial cell is also known to suppress xenogeneic T cells (Th22 cell) (non-patent document 5), and it is known that retinal pigment epithelial cell itself has an immunosuppressive function, due to which the environment around retinal pigment epithelial cell tends to suppress immune reaction. Also, it is known that coculture of a human retinal pigment epithelial cell pre-treated with IFN-γ or macrophage with allogeneic T cells activates T cells since production of IL-2 and the like increases (non-patent document 6). IFN-γ is also known to play an important role in the expression of MHC class II molecule (non-patent document 7). However, an allogeneic transplantation strategy in consideration of HLA compatibility has not existed to date in the transplantation to retina disease patients by using a retinal pigment epithelial cell (hereinafter to be indicated as "RPE cell").

DOCUMENT LIST

Non-Patent Documents non-patent document 1: Sugita S et al, J Immunol. 2004, 172: 4184-4194.
non-patent document 2: Sugita S et al, J Immunol. 2006, 176: 118-127.
non-patent document 3: Sugita S et al, J Immunol, 2008, 181: 7525-7536.
non-patent document 4: Sugita S et al, J Immunol, 2009, 183: 5013-5022.
non-patent document 5: Sugita S et al, IOVS, 2013, vol. 54, No. 10: 6926-6933.
non-patent document 6: Enzmann V et al. Graefes Arch Clin Exp Ophthalmol. 2001 July; 239(6):445-51
non-patent document 7: Enzmann V. Transplant Immunology 7:9-14, 1999

SUMMARY OF THE INVENTION

Problems to be Solved by the Invention

An object of the present invention is to provide an agent for treating ophthalmic diseases and a screening method for an agent for treating ophthalmic diseases and the like. Another object of the present invention is to provide a method for predicting immunorejection response associated with transplantation of retinal pigment epithelial cell in patients with ophthalmic diseases.

Means of Solving the Problems

The present inventors obtained T cells from plural test subjects and iPS cell-derived retinal pigment epithelial (RPE) cells, performed HLA typing and then contact culture of the aforementioned T cells and RPE cells, and measured the concentration of cytokine produced from the T cells to find that, when the alleles of 3 gene loci of HLA-A, HLA-B and HLA-DR of the aforementioned T cells match with the alleles at respective 3 gene loci of HLA-A, HLA-B and HLA-DR of a retinal pigment epithelial cell wherein the genotype of the 3 gene loci is each homozygous, the cytokine concentration is equal to or lower than that of the T cell alone.

The present inventors have conducted further studies based on these findings and completed the present invention.

Accordingly, the present invention relates to the following.

[1] A therapeutic agent for ophthalmic diseases, comprising a retinal pigment epithelial cell having an HLA-A gene locus, an HLA-B gene locus and an HLA-DR gene locus, wherein each locus has a homozygous genotype, which agent is for a patient with an ophthalmic disease and having a combination wherein at least one of the alleles at each corresponding gene locus is the same as an allele at the gene locus of the retinal pigment epithelial cell.

[2] The agent of [1], which suppresses an immunorejection response after transplantation.

[3] The agent of [1] or [2], wherein the retinal pigment epithelial cell is derived from a pluripotent stem cell.
[4] The agent of [3], wherein the pluripotent stem cell is an iPS cell.
[5] The agent of any one of [1]-[4], wherein the ophthalmic disease is retina denaturation or a disease associated with retina denaturation.
[6] A method of selecting a therapeutic agent for an ophthalmic disease for a patient with the ophthalmic disease, comprising
(i) a step of examining genotypes of HLA-A gene locus, HLA-B gene locus and HLA-DR gene locus of patient-derived T cells,
(ii) a step of selecting a retinal pigment epithelial cell having an allele matching the allele at each gene locus clarified in step (i).
[7] The method of [6], wherein the retinal pigment epithelial cell in step (ii) has an HLA-A gene locus, an HLA-B gene locus and an HLA-DR gene locus, and a genotype of each locus is homozygous.
[8] A method of selecting a therapeutic agent for ophthalmic diseases, which is for a patient with an ophthalmic disease, comprising
(1) a step of performing contact culture of patient-derived T cells with retinal pigment epithelial cells,
(2) a step of measuring a concentration of inflammatory cytokine secreted in the culture supernatant in step (1), and
(3) a step of judging that the retinal pigment epithelial cell can be used as an active ingredient of a therapeutic agent for ophthalmic diseases of a patient, when the inflammatory cytokine concentration in step (2) is of the same level as or not more than a concentration of an inflammatory cytokine in a culture supernatant obtained by culturing the patient-derived T cells alone.
[9] The method of [8], wherein the retinal pigment epithelial cell has an HLA-A gene locus, an HLA-B gene locus and an HLA-DR gene locus, and a genotype of each locus is homozygous.
[10] The method of [8] or [9], wherein the patient-derived T cells in step (1) are activated using an anti-CD3 antibody.
[11] The method of any one of [8]-[10], wherein the patient-derived T cells in step (1) are CD4 positive, and the inflammatory cytokine measured in step (2) is IFN-γ.
[12] The method of any one of [8]-[10], wherein the patient-derived T cells in step (1) are CD8 positive, and the inflammatory cytokine measured in step (2) is Granzyme B.
[13] A test method for predicting a rejection response in an ophthalmic disease patient to be transplanted with a retinal pigment epithelial cell for transplantation, comprising
(A) a step of performing contact culture of patient-derived T cells with said retinal pigment epithelial cells,
(B) a step of measuring a concentration of inflammatory cytokine secreted in the culture supernatant in step (A), and
(C) a step of judging that a rejection response to the retinal pigment epithelial cell occurs, when the inflammatory cytokine concentration in step (B) is significantly higher than a concentration of an inflammatory cytokine in a culture supernatant obtained by culturing the patient-derived T cells alone.
[14] The method of [13], wherein the retinal pigment epithelial cell for transplantation has an HLA-A gene locus, an HLA-B gene locus and an HLA-DR gene locus, and a genotype of each locus is homozygous.
[15] The method of [13] or [14], wherein the patient-derived T cells in step (A) are activated using an anti-CD3 antibody.
[16] The method of any one of [13]-[15], wherein the patient-derived T cells in step (A) are CD4 positive, and the inflammatory cytokine measured in step (B) is IFN-γ.
[17] The method of any one of [13]-[15], wherein the patient-derived T cells in step (A) are CD8 positive, and the inflammatory cytokine measured in step (B) is Granzyme B.
[18] A method of treating an ophthalmic disease, comprising forming a sheet of a retinal pigment epithelial cell having an HLA-A gene locus, an HLA-B gene locus and an HLA-DR gene locus, wherein each locus has a homozygous genotype, and transplanting the sheet to a patient with an ophthalmic disease and having a combination wherein at least one of the alleles at each corresponding gene locus is the same as an allele at the gene locus of the retinal pigment epithelial cell.
[19] The method of [18], wherein the retinal pigment epithelial cell is derived from a pluripotent stem cell.
[20] The method of [19], wherein the pluripotent stem cell is an iPS cell.
[21] The method of any one of [18]-[20], wherein the ophthalmic disease is retina denaturation or a disease associated with retina denaturation.
[22] A retinal pigment epithelial cell having an HLA-A gene locus, an HLA-B gene locus and an HLA-DR gene locus, wherein each locus has a homozygous genotype, which cell is for use for the treatment of an ophthalmic disease of a patient with an ophthalmic disease and having a combination wherein at least one of the alleles at each corresponding gene locus is the same as an allele at the gene locus of the retinal pigment epithelial cell.
[23] The retinal pigment epithelial cell of [22], wherein the retinal pigment epithelial cell is derived from a pluripotent stem cell.
[24] The retinal pigment epithelial cell of [23], wherein the pluripotent stem cell is an iPS cell.
[25] The retinal pigment epithelial cell of any one of [22]-[24], wherein the ophthalmic disease is retina denaturation or a disease associated with retina denaturation.
[26] A retinal pigment epithelial cell having an HLA-A gene locus, an HLA-B gene locus and an HLA-DR gene locus, wherein each locus has a homozygous genotype, which cell is for use for the production of a therapeutic agent for an ophthalmic disease of a patient with an ophthalmic disease and having a combination wherein at least one of the alleles at each corresponding gene locus is the same as an allele at the gene locus of the retinal pigment epithelial cell.
[27] The retinal pigment epithelial cell of [26], wherein the retinal pigment epithelial cell is derived from a pluripotent stem cell.
[28] The retinal pigment epithelial cell of [27], wherein the pluripotent stem cell is an iPS cell.
[29] The retinal pigment epithelial cell of any one of [26]-[28], wherein the ophthalmic disease is retina denaturation or a disease associated with retina denaturation.

Effect of the Invention

In conventional allogeneic transplantation, the HLA type of a donor and that of a recipient are requested to match as far as possible. Particularly, in bone marrow transplantation, it is considered necessary to match all alleles of 6 gene loci antigens known as HLA type. According to the present invention, however, when the genotype of 3 gene loci of HLA-A, HLA-B and HLA-DR on the donor side is homozygous in RPE cell transplantation, rejection response can be suppressed by merely matching one of the HLA loci of the recipient. Since immunologically incompatible cells for transplantation can be distinguished and selected by previously collecting blood samples from the patient, the burden on patients can be reduced by avoiding incompatible cells for transplantation. RPE cells selected by this method can be used for transplantation.

In addition, the present invention used to determine whether an immunosuppressant is necessary can contribute to the selection of a treatment plan. Thus, the present invention contributes to marked improvement of treatment efficiency by allogeneic transplantation, and also affords effects such as reduction of the preparation costs of cells unsuitable for transplantation and the like.

RPE cells wherein the genotype of 3 gene loci of HLA-A, HLA-B and HLA-DR is homozygous can be used as a therapeutic agent for ophthalmic diseases for patients having a combination wherein at least one of the alleles at the 3 gene loci matches with the allele of the retinal pigment epithelial cell.

DESCRIPTION OF EMBODIMENTS

Figure 1:
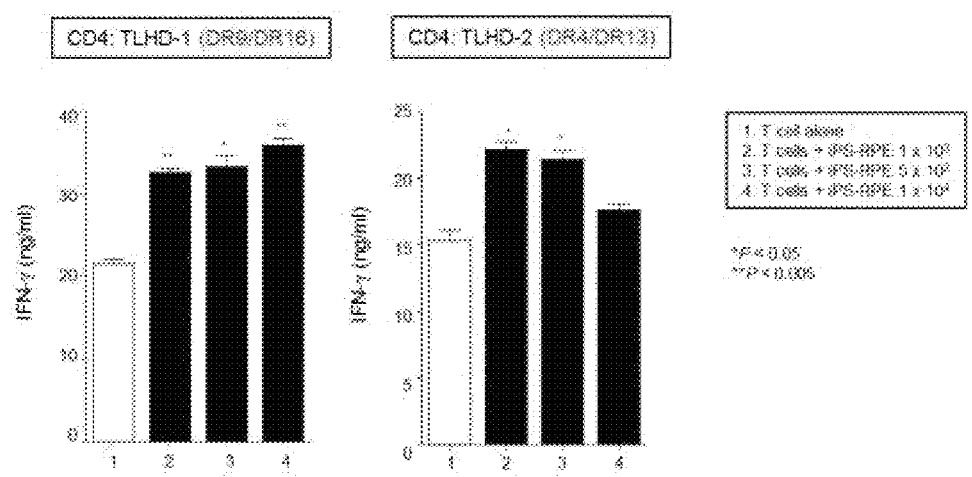
FIG. 1 shows the concentration of IFN-γ in a culture supernatant when CD4 positive T cell suspension (TLHD-1, TLHD-2) and 454E2-iPS-derived RPE cells were cocultured.

The present invention provides a therapeutic agent for ophthalmic diseases, comprising a retinal pigment epithelial cell having an HLA-A gene locus, an HLA-B gene locus and an HLA-DR gene locus, wherein each locus has a homozygous genotype, which agent is for a patient with an ophthalmic disease and having a combination wherein at least one of the alleles at each corresponding gene locus is the same as an allele at the gene locus of the retinal pigment epithelial cell (hereinafter to be referred to as "the therapeutic agent of the present invention").

The therapeutic agent of the present invention contains a retinal pigment epithelial cell. The "retinal pigment epithelial cell" in the present invention refers to an epithelial cell constituting the retinal pigment epithelium, and a progenitor cell thereof. Whether a retinal pigment epithelial cell or not can be confirmed by, for example, expression of cell markers (RPE65, CRALBP, MERTK, BEST1 etc.), cell forms (intracellular melanin dye deposition, polygonal and flat cell form, formation of polygonal actin bundle etc.) and the like. The progenitor cell of retinal pigment epithelial cell means a cell directed to be induced to differentiate into retinal pigment epithelial cell, and whether a progenitor cell or not can be confirmed by expression of cell markers (Mitf, Pax6, Rx, Crx etc.) and the like. Functional evaluation of retinal pigment epithelial cell can be confirmed using, for example, secretability of cytokine (VEGF, PEDF etc.), phagocytic capacity or the like as an index. These functional evaluation and confirmation operations can be performed by those of ordinary skill in the art by setting appropriate conditions.

As the retinal pigment epithelial cell in the present invention, retinal pigment epithelial cells derived from a mammal can be used. Examples of the mammal include mouse, rat, guinea pig, hamster, rabbit, cat, dog, sheep, swine, bovine, horse, goat, monkey and human. Human retinal pigment epithelial cell is preferably used when retinal pigment epithelial cells are produced for the purpose of transplanting to human, and the like.

The aforementioned "retinal pigment epithelial cell" may be a primary cell collected directly, or a cell after passage for several generations. The primary retinal pigment epithelial cell can be isolated by a known method and, for example, retinal pigment epithelial cell can be obtained by isolating an eyeball from a dead body, quickly dividing the eyeball at the equator part, removing vitreous body and retina, treating them as necessary with collagenase, hyaluronidase etc., and recovering the cells by abrasion with a cell scraper or detaching them from the Bruch's membrane with trypsin or EDTA solution, after which the cells are stood in a culture medium, induced to adhere and grow on a culture dish to achieve the growth thereof in a necessary amount, which is followed by appropriate passage by a trypsin treatment and the like to ensure the cell number.

Furthermore, the aforementioned "retinal pigment epithelial cell" may be a cell obtained by differentiation induction of a stem cell including somatic stem cells such as pluripotent stem cell, neural stem cell and the like, or a progenitor cell including neural progenitor cell, retina progenitor cell, and a cell obtained by differentiation induction of a pluripotent stem cell is preferable.

The "pluripotent stem cell" in the present invention means a stem cell having self-replication competence and differentiation pluripotency and is not particularly limited. For example, embryonic stem cells (ES cells), iPS cells (induced pluripotent stem cells) and the like are widely utilized. Preferably, human ES cell or human iPS cell is utilized, and a human iPS cell is more preferably utilized.

The "iPS cell" in the present invention means a cell that artificially acquired self-replication competence and differentiation pluripotency by contacting a nuclear reprogramming factor with a somatic cell (e.g., fibroblast, skin cell, lymphocyte etc.). iPS cell was found for the first time by a method including introduction of a nuclear reprogramming factor consisting of Oct3/4, Sox2, Klf4 and c-Myc into a somatic cell (e.g., fibroblast, skin cell etc.). (Cell, 126: p. 663-676, 2006). Thereafter, many researchers are working on various improvements in the combination of reprogramming factors and introduction method of factors, and a variety of production methods of induced pluripotent stem cell have been reported. However, the production method of iPS cell in the present invention is not particularly limited.

In the "retinal pigment epithelial cell" in the present invention, the genotype of HLA-A gene locus, HLA-B gene locus and HLA-DR gene locus is preferably each homozygous. The genotype being homozygous means that two alleles are genes having the same base sequence. In the below-mentioned Examples, retinal pigment epithelial cells obtained by differentiation induction of T cells and iPS cells collected from a test subject were cocultured and it was found that T cells having a combination wherein at least one of the alleles at each corresponding gene locus is the same as an allele at the gene locus of the retinal pigment epithelial cell having an HLA-A gene locus, an HLA-B gene locus and an HLA-DR gene locus, wherein each locus has a homozygous genotype, shows the same level of cytokine production as the control (T cells alone), or surprisingly suppressed cytokine production.

Conventionally, it is known that retinal pigment epithelial cell expresses a molecule suppressing inflammatory cells including T cells, and affords a promotive signal on regulatory T cells. However, many of these are the results on allogeneic autologous cells (e.g., non-patent documents 1-4 in Background Art). On the other hand, the present inventors have reported that retinal pigment epithelial cells suppress xenogeneic T cells (e.g., non-patent document 5 in Background Art); however, this simply shows the function of retinal pigment epithelial cell itself. In fact, in xenogeneic transplantation, an acute rejection response poses a huge problem and, since retinal pigment epithelial cell does not present an antigen, these reports by the present inventors do not suggest the present invention at all.

From the foregoing, when the genotype of 3 gene loci of HLA-A, HLA-B and HLA-DR on the donor side is homozygous in retinal pigment epithelial cell transplantation, rejection response can be suppressed by merely matching one allele of the HLA gene loci of the recipient, and cells for transplantation can be rapidly supplied to ophthalmic disease patients in need of retinal pigment epithelial transplantation. The present invention is an invention completed based on the finding that when the genotype of 3 gene loci of HLA-A, HLA-B and HLA-DR on the donor side is homozygous in allogeneic retinal pigment epithelial cell transplantation, rejection response can be suppressed by merely matching one of the HLA loci of the recipient, and the finding is highly significant. The final object of the present invention is to suppress immunorejection response that may occur in allogeneic transplantation of retinal pigment epithelial cells as much as possible. From such aspects, a retinal pigment epithelial cell having an HLA-A gene locus, an HLA-B gene locus and an HLA-DR gene locus, wherein each locus has a homozygous genotype, which is the active ingredient of a therapeutic agent for ophthalmic diseases to be administered to ophthalmic disease patients in the present invention is an allogeneic cell, and a retinal pigment epithelial cell suitable for the patient is selected from various retinal pigment epithelial cells wherein a genotype of the gene locus is homozygous.

The genotype of HLA-A gene locus, HLA-B gene locus and HLA-DR gene locus of T cells obtained from a patient with an ophthalmic disease can be examined by a known method and, for example, as shown in the Examples below, and can be easily so determined by performing HLA typing. In addition, the genotype at each gene locus of the retinal pigment epithelial cell to be used for the agent of the present invention can also be examined by a similar method. A use method is desirable in which various retinal pigment epithelial cells whose genotype at each gene locus is homozygous and whose specific allele has previously been clarified are stocked, and a cell appropriate for a patient with an ophthalmic disease is selected and used therefrom.

Examples of the ophthalmic diseases to which the therapeutic agent of the present invention can be applied include retina denaturation and diseases associated with retina denaturation. Examples of the retina denaturation and diseases associated with retina denaturation include retina denaturation diseases such as age-related macular degeneration, retinitis pigmentosa, diabetic retinopathy, retinal detachment and the like.

The ophthalmic disease patients to whom the therapeutic agent of the present invention can be applied are preferably ophthalmic disease patients having a combination wherein at least one of the alleles at each corresponding gene locus is the same as an allele which is homozygous at the HLA-A gene locus, HLA-B gene locus and HLA-DR gene locus of the retinal pigment epithelial cell.

The range of ophthalmic disease site to which the therapeutic agent of the present invention can be applied is appropriately determined according to the target disease, animal species, age, sex, body weight, symptom of the subject of administration, and the like.

As a use method of the therapeutic agent of the present invention, it can be transplanted in a sheet form. A method of forming a sheet of a retinal pigment epithelial cell is known and, for example, is described in WO 2012/115244. A retinal pigment epithelial cell sheet may be transplanted at once or several times by portions. The number of transplantations to be applied is determined according to the disease and according to the medical workers and guideline. For example, when the disease is age-related macular degeneration, a cell sheet for transplantation may be transplanted twice or more according to the severity. When transplantation is to be performed plural times, the interval is not particularly limited and a period of several days—several weeks may be provided. Alternatively, the therapeutic agent of the present invention with the cells dispersed therein may be directly transplanted to the target site. The number of transplantation to be applied is determined according to the guideline and the like, similar to the case of sheet, and the transplantation period and the like are also determined as appropriate, similar to the case of sheet.

The present invention also provides a method of selecting a therapeutic agent for ophthalmic diseases for ophthalmic disease patients.

Specifically, the method of selecting a therapeutic agent for ophthalmic diseases of the present invention (hereinafter to be referred to as "the method (1) of the present invention") includes the following steps:
(i) a step of examining genotypes of HLA-A gene locus, HLA-B gene locus and HLA-DR gene locus of patient-derived T cells,
(ii) a step of selecting a retinal pigment epithelial cell having an allele matching the allele at each gene locus clarified in step (i).

In the method (1) of the present invention, step (i), the genotype of HLA-A gene locus, HLA-B gene locus and HLA-DR gene locus of T cells obtained from a patient with an ophthalmic disease can be examined by a known method and, for example, as shown in the Examples below, and can be easily determined by performing HLA typing. The ophthalmic disease of the a patient from which T cells in the method (1) of the present invention derived may be the same as the ophthalmic diseases to be the application target of the therapeutic agent of the present invention.

The retinal pigment epithelial cell having an allele matching the allele at each gene locus clarified in step (i), which is selected in the method (1) of the present invention, step (ii), is useful as a therapeutic agent for ophthalmic diseases that does not cause rejection response on application to ophthalmic disease patients. In the method (1) of the present invention, genotypes of HLA-A gene locus, HLA-B gene locus and HLA-DR gene locus of the retinal pigment epithelial cell are each preferably homozygous. The retinal pigment epithelial cell in the method (1) of the present invention may be prepared in the same manner as in the preparation of the retinal pigment epithelial cell to be contained in the therapeutic agent of the present invention.

The present invention also provides a method of selecting a therapeutic agent for ophthalmic diseases for other ophthalmic disease patients.

Specifically, the method of selecting a therapeutic agent for ophthalmic diseases of the present invention (hereinafter to be referred to as "the method (2) of the present invention") includes the following steps:
(1) a step of performing contact culture of patient-derived T cells with retinal pigment epithelial cells,
(2) a step of measuring a concentration of inflammatory cytokine secreted in the culture supernatant in step (1), and
(3) a step of judging that the retinal pigment epithelial cell can be used as an active ingredient of a therapeutic agent for ophthalmic diseases of a patient, when the inflammatory cytokine concentration in step (2) is of the same level as or not more than a concentration of an inflammatory cytokine in a culture supernatant obtained by culturing the patient-derived T cells alone.

In the method (2) of the present invention, step (1), the contact culture of the patient-derived T cells and retinal pigment epithelial cell can be performed according to the method described in the below-mentioned Examples. Specifically, the patient-derived T cells are seeded in a 96 well plate, retinal pigment epithelial cells are added and the mixture is cultured. In this step, the patient-derived T cells may be activated in advance. While an activating method of T cells is not particularly limited, for example, an anti-CD3 antibody may be added. T cells may be prepared by separating to CD4 positive cells and CD8 positive cells in advance.

The retinal pigment epithelial cells to be used in this step may be radiation-treated in advance to avoid growth of retinal pigment epithelial cell in the culture. Furthermore, genotypes of HLA-A gene locus, HLA-B gene locus and HLA-DR gene locus of the retinal pigment epithelial cell to be used for the culture are each preferably homozygous.

A culture medium can be used without any particular limitation as long as it is a medium for cell culture which is generally used in the pertinent field. For example, basal media such as F-10 medium, F12 medium, MEM, BME medium, DMEM, αMEM, IMD medium, ES medium, DM-160 medium, Fisher medium, WE medium and RPMI1640 medium and the like can be used. Furthermore, serum (fetal bovine serum etc.), various growth factors (EGF, FGF, HGF, PDGF and the like), antibiotic, amino acid and the like may be added to the basal medium as necessary. The pH of the medium is preferably about 6-about 8. The culture can be performed, for example, generally at about 30-about 40° C. for about 15-about 60 hr, preferably 48 hr. For the culture, the ratio of the patient-derived T cells and the retinal pigment epithelial cells is generally 500:1-10:1, preferably 400:1-25:1, more preferably 200:1-50:1. By setting the ratio of the cell number of the patient-derived T cells and retinal pigment epithelial cells within this range, T cells secrete an appropriate amount of inflammatory cytokine or cell injury substance, which enables more definite determination of whether the retinal pigment epithelial cell to be the target can be applied to the patients.

The ophthalmic disease of a patient to be the derivation of the T cells in the method (2) of the present invention may be the same as the ophthalmic disease to be the application target of the therapeutic agent of the present invention, and the retinal pigment epithelial cell may be prepared in the same manner as the retinal pigment epithelial cell to be contained in the therapeutic agent of the present invention.

In step (2) of the method (2) of the present invention, the concentration of inflammatory cytokine secreted in the culture supernatant can be measured according to the method described in the below-mentioned Examples. To be specific, it can be measured by ELISA, Western blot, FACS and the like. The inflammatory cytokine to be measured in this step is not particularly limited as long as it is involved in the rejection response. For example, when CD4 positive cell is used as the patient-derived T cell in step (1), IFN-γ, IL-17 and TNF-α can be mentioned, of which IFN-γ is more preferable. When CD8 positive cell is used as the patient-derived T cell in step (1), Granzyme B, Perforin and TNF-α can be mentioned, of which Granzyme B is more preferable.

As shown in the below-mentioned Examples, retinal pigment epithelial cells obtained by differentiation induction of T cells and iPS cells collected from a test subject were cocultured, and it was found that T cells having a combination wherein at least one of the alleles at each corresponding gene locus is the same as an allele at said gene locus of the retinal pigment epithelial cell having an HLA-A gene locus, an HLA-B gene locus and an HLA-DR gene locus, wherein each locus has a homozygous genotype, shows the same level of cytokine production as the control, or suppressed cytokine production. Therefore, in step (3) of the method (2) of the present invention, it can be judged that the retinal pigment epithelial cell can be used as an active ingredient of a therapeutic agent for ophthalmic diseases of a patient, when the inflammatory cytokine concentration measured in step (2) is of the same level as or not more than a concentration of an inflammatory cytokine in a culture supernatant obtained by culturing the patient-derived T cells alone.

The present invention also provides a test method for predicting a rejection response in an ophthalmic disease patient to be transplanted with a retinal pigment epithelial cell for transplantation. Specifically, the test method for predicting a rejection response of the present invention (hereinafter to be referred to as "the method (3) of the present invention") includes the following steps:
(A) a step of performing contact culture of patient-derived T cells with said retinal pigment epithelial cells,
(B) a step of measuring a concentration of inflammatory cytokine secreted in the culture supernatant in step (A), and
(C) a step of judging that a rejection response to the retinal pigment epithelial cell occurs, when the inflammatory cytokine concentration in step (B) is significantly higher than a concentration of an inflammatory cytokine in a culture supernatant obtained by culturing the patient-derived T cells alone.

Steps (A) and (B) of the method (3) of the present invention can be performed similarly to steps (1) and (2) of the method (2) of the present invention. As shown in the below-mentioned Examples, retinal pigment epithelial cells obtained by differentiation induction of T cells and iPS cells collected from a test subject were cocultured, and it was found that T cells having a combination wherein at least one of the alleles at each corresponding gene locus is not the same as an allele at said gene locus of the retinal pigment epithelial cell having an HLA-A gene locus, an HLA-B gene locus and an HLA-DR gene locus, wherein each locus has a homozygous genotype, shows higher cytokine production than the control. Therefore, in step (C) of the method (3) of the present invention, it can be judged that a rejection response to the retinal pigment epithelial cell occurs, when the inflammatory cytokine concentration in step (B) is significantly higher than a concentration of an inflammatory cytokine in a culture supernatant obtained by culturing the patient-derived T cells alone.

EXAMPLES

The present invention is explained in more detail in the following by referring to Examples, which are mere exemplifications and do not limit the scope of the present invention in any way.

(Preparation Example 1) Preparation of Human iPS Cell-Derived RPE Cells

Using iPS cell line 454E2 or 453F2 (provided by Kyoto University) disclosed in Nature Methods 8, 409-412 2011 as iPS cells, and according to of the differentiation induction method described in J Cell Sci (2009) 122: 3169-3179, 454E2-iPS cell-derived RPE cells and 453F2-iPS cell-derived RPE cells (both cells have homozygous genotype at HLA-A, -B, -DR3 gene loci) were prepared.

In addition, using, as iPS cell line, iPS cells established from human skin-derived fibroblast of a test subject name TLHD-1 according to the method described in Nature (2011) 474: 225-229 instead of 454E2 or 453F2, TLHD-1-iPS cell-derived RPE cells were prepared by a similar method.

(Preparation Example 2) Preparation of Human T Cell Suspension

CD4 positive T cells and CD8 positive T cells were separated from human peripheral blood (test subject names; TLHD-1-TLHD-22) by using a MACS magnetic cell sorter, suspended in 100 U/ml rhIL-2-containing RPMI culture medium (RPMI 1640 445 ml, FBS 50 ml, penicillin-streptomycin 5 ml) to prepare each cell suspension.

(Reference 1) HLA Typing

The results of HLA typing of the cells used in Examples 1-8 by a conventional method are shown in the following Table. The results of HLA typing of respective T cells of test subjects obtained in Preparation Example 2 are shown in Tables 1-1, 1-2, and the results of HLA typing of the human iPS-derived RPE cells of Preparation Example 1 and those induced from other iPS cells are shown in Table 2.

Relative to 454E2-iPS cell-derived RPE cells (homozygous at 3 gene loci of HLA-A, HLA-B, HLA-DR), the test subject names TLHD-10 and TLHD-21 had the same alleles in the genotype of 3 gene loci of HLA-A, HLA-B, HLA-DR, the test subject names TLHD-6, 18 had the same alleles in the genotype of 2 gene loci of HLA-B, HLA-DR, the test subject names TLHD-2, 5, 7, 9, 11, 12, 13, 14, 15, 17, 20, 22 had the same alleles only in the genotype of 1 gene locus of HLA-A, and the test subject name TLHD-19 had the same alleles only in the genotype of 1 gene locus of HLA-DR.

Relative to 453F2-iPS cell-derived RPE cells (homozygous at 3 gene loci of HLA-A, HLA-B, HLA-DR), the test subject names TLHD-1, 4, 18 had the same alleles only in the genotype of 2 gene loci, and the test subject name TLHD-6 had the same alleles only in the genotype of 1 gene locus of HLA-A.

TABLE 1

| No. | T cells | Origin | HLA-A | HLA-B | HLA-DRB1 | T cell response to 454E2* | HLA-matched to 454E2 |
|---|---|---|---|---|---|---|---|
| 1 | TLHD1 | PBMCs | A11/— (11:01/—) | B62/B67 (15:01/67:01) | DR9/DR16 (09:01/16:02) | CD4 (+)/CD8 (+) | |
| 2 | TLHD2 | PBMCs | A24/33 (24:02/33:03) | B44/B55 (44:03/55:02) | DR4/DR13 (04:05/13:02) | CD4 (+)/CD8 (−) | A24:02 |
| 3 | TLHD3 | PBMCs | A2/A26 (02:01/26:03) | B44/B61 (40:06/44:03) | DR4/DR8 (04:05/08:03) | CD4 (+)/CD8 (+) | DQB1 06:01 |
| 4 | TLHD4 | PBMCs | A2/A3 (02:01/03:01) | B62/B51 (15:01/51:01) | DR4/DR4 (04:02/04:06) | CD4 (+)/CD8 (+) | |
| 5 | TLHD5 | PBMCs | A24/A33 (24:02/33:03) | B7/B44 (07:02/44:03) | DR1/DR13 (01:01/13:02) | CD4 (+)/CD8 (+) | A24:02 |
| 6 | TLHD6 | PBMCs | A11/A26 (11:01/26:02) | B39/B52 (39:01/52:01) | DR8/DR15 (08:03/15:02) | CD4 (−)/CD8, nt | B52:01 DRB1 15:02 |
| 7 | TLHD7 | PBMCs | A24/A26 (24:02/26:01) | B35/B54 (35:01/54:01) | DR14/DR15 (14:05/15:01) | CD4 (+)/CD8, nt | A24:02 |
| 8 | TLHD8 | PBMCs | A26/A26 (26:01/26:03) | B13/B35 (13:01/35:01) | DR12/DR15 (12:02/15:01) | CD4 (+)/CD8 (+) | |
| 9 | TLHD9 | PBMCs | A24/A26 (24:02/26:03) | B51/B54 (51:01/54:01) | DR4/DR12 (04:05/12:01) | CD4 (+)/D38, nt | A24:02 |
| 10 | TLHD10 | PBMCs | A24/A31 (24:02/31:01) | B61/B52 (40:02/52:01) | DR15/DR15 (15:01/15:02) | CD4 (−)/CD8 (−) | A24:02/B52:01 DRB1 15:02 |
| 11 | TLHD11 | PBMCs | A24/— (24:02/—) | B7/B59 (07:02/59:01) | DR4/DR9 (04:05/09:01) | CD4, nt/CD8 (−) | A24:02 |
| 12 | TLHD12 | PBMCs | A24/A26 (24:02/26:01) | B51/B54 (51:01/54:01) | DR14/DR14 (14:03/14:05) | CD4, nt/CD8 (−) | A24:02 |
| 13 | TLHD13 | PBMCs | A24/A26 (24:02/26:01) | B61/B56 (40:02/56:01) | DR4/DR14 (04:05/14:54) | CD4 (+)/CDS (−) | A24:02 |

TABLE 1-continued

| No. | T cells | Origin | HLA-A | HLA-B | HLA-DRB1 | T cell response to 454E2* | HLA-matched to 454E2 |
|---|---|---|---|---|---|---|---|
| 14 | TLHD14 | PBMCs | A1/A24 (01:01/24:02) | B37/B51 (37:01/51:01) | DR9/DR19 (09:01/10:01) | CD4 (+)/CD8 (−) | A24:02 |
| 15 | TLHD15 | PBMCs | A2/A24 (02:01/24:02) | B48/B54 (48:01/54:01) | DR4/— (04:05/—) | CD4, nt/CD8, nt | A24:02 |
| 16 | TLHD16 | PBMCs | A2/A31 (02:01/31:01) | B62/B61 (15:01/40:02) | DR9/— (09:01/—) | CD4 (+)/CD8 (+) | |
| 17 | TLHD17 | PBMCs | A24/A31 (24:02/31:01) | B54/B55 (54:01/55:02) | DR4/DR9 (04:05/09:01) | CD4 (+)/CD8 (−) | A24:02 |
| 18 | TLHD18 | PBMCs | A2/A11 (02:01/11:01) | B62/B52 (15:01/52:01) | DR14/DR15 (14:54/15:02) | CD4 (−)/CD8 (−) | B52:01 DRB1 15:02 |
| 19 | TLHD19 | PBMCs | A2/A33 (02:01/33:03) | B35/B44 (35:01/44:03) | DR13/DR15 (13:02/15:02) | CD4 (−)/CD8 (+) | DRB1 15:02 |
| 20 | TLHD20 | PBMCs | A2/A24 (02:01/24:02) | B44/B51 (44:03/51:01) | DR9/DR13 (09:01/13:02) | CD4 (+)/CD8 (+) | A24:02 |
| 21 | TLHD21 | PBMCs | A24/A24 (24:02/24:20) | B39/B52 (39:01/52:01) | DR9/DR15 (09:01/15:02) | CD4 (−)/CD8 (−) | A24:02/B52:01 DRB1 15:02 |
| 22 | TLHD22 | PBMCs | A24/A26 (24:02/26:02) | B39/B61 (39:01/40:06) | DR8/DR14 (08:03/14:06) | CD4 (−)/CD8 (+) | A24:02 |

*T cell response to 454E2: Cytokine concentration when each T cell (CD4 positive or CD8 positive) is cultured without retinal pigment epithelial cell is taken as control, concentration higher than that is (+) and concentration the same as or lower than that is (−). nt shows not measured.

TABLE 2

| No. | RPE and control cells | Origin | HLA-A | HLA-B | HLA-DR | Reference |
|---|---|---|---|---|---|---|
| 1 | 836B1 iPS-RPE cells | iPS cells (skin fibroblasts from HD) | A2/— (02:01/—) | B27/B50 (27:03/50:01) | DR1/13 (01:01/13:03) | |
| 2 | 101G26 iPS-RPE cells | iPS cells (skin fibroblast from RP) | A11/A24 (11:01/24:02) | B60/B54 (40:01/54:01) | DR4/DR8 (04:05/08:03) | |
| 3 | 454E2 iPS-RPE cells | iPS cells (dental pulp cells from HD) | A24/— (24:02/—) | B52/— (52:01/—) | DR15/— (15:02/—) | HLA homozygous donor |
| 4 | 453F2 iPS-RPE cells | iPS cells (dental pulp cells from HD) | A11/— (11:01/—) | B62/— (15:01/—) | DR4/— (04:06/—) | HLA homozygous donor |
| 5 | TLHD1 iPS-RPE cells | iPS cells (skin fibroblasts from HD) | A11/— (11:01/—) | B62/B67 (15:01/67:01) | DR9/DR16 (09:01/16:02) | Autologous TLHD1 |
| 6 | ES-RPE cells | ES cells | A2/A24 (02:06/24:02) | B35/B39 (35:01/39:01) | DR9/DR14 (09:01/14:05) | |
| 7 | Primary RPE cells | Fetal ocular cells | A3/A24 (03:01/24:02) | B35/B60 (35:01/40:01) | DR1/— (01:01/—) | |
| 8 | RPE cell lines (ARPE19) | Adult ocular cells | A2/A3 (02:01/03:01) | B7/B65 (07:02/14:02) | DR13/DR15 (13:02/15:01) | |
| 9 | Cornea endothelial cells | Primary human CE cells | A24/A68 (24:02/68:01) | B27/B51 (27:03/51:01) | DR7/DR11 (07:01/11:01) | |
| 10 | Fibroblast cells | Skin tissues (HD) | A24/A26 (24:02/26:02) | B61/B52 (40:02/52:01) | DR9/DR15 (09:01/15:02) | |

(Preparation Example 3) Preparation of Monkey iPS Cell-Derived RPE Cells iPS cells were established from the fibroblast derived from the skin of *Macaca fascicularis* according to the method described in Nature (2011) 474: 225-229 (GLIS1use), and monkey iPS cell-derived RPE cells were prepared according to the differentiation induction method described in J Cell Sci (2009) 122: 3169-3179 from each of normal monkeys (A, B) and a disease model monkey (C) prepared by forming a retinal photocoagulation spot in one eye by retinal photocoagulation procedure.

(Preparation Example 4) Preparation of Monkey T Cell Suspension

CD4 positive T cells and CD8 positive T cells were separated from the peripheral blood of the disease model monkey (C) by using a MACS magnetic cell sorter, and suspended in 100 U/ml rhIL-2-containing RPMI culture medium (RPMI 1640 445 ml, FBS 50 ml, penicillin-streptomycin 5 ml) to prepare each T cell suspension.

(Reference 2) MHC Typing

MHC typing of the cells used in Examples 9, 10 was performed by a conventional method. The disease model monkey (C) had the same alleles at 3 gene loci relative to iPS cell-derived RPE cells (homozygous at 3 gene loci from among Mafa-A, -B, -DRA, -DRB, -DQA, -DQB, -DPA, -DPB gene loci) of normal monkey A. The iPS cell-derived RPE cells of the normal monkey B were different in all genotypes of MHC from the disease model monkey (C).

Example 1

In a 96 well plate, an anti-CD3 antibody (1 μg/ml) was added to CD4 positive T cell suspensions (TLHD-1 and TLHD-2) obtained in Preparation Example 2 and the suspensions were dispensed to the well at a concentration of $5 \times 10^5$ cells/well. 454E2-iPS-derived RPE cells obtained in Preparation Example 1 were added to each well at 3 concentrations of 1×10³/well, 5×10³/well, 1×10⁴/well, and cultured, wherein the suspension so without addition was used as a control. After culture for 48 hr, the culture supernatant was recovered, and the concentration of IFN-γ in the culture supernatant was measured by ELISA. The results are shown in FIG. 1.

As a result, both TLHD-1 and TLHD-2 showed an increased production of IFN-γ at all 3 kinds of concentrations as compared to the control. Therefore, transplantation of 454E2-iPS-derived RPE cells to test subjects TLHD-1 and TLHD-2 can be judged to have a high possibility of causing a rejection response.

HLA antigens of TLHD-1 and TLHD-2 showed different haplotype from that of HLA-DR antigen (Class-II) of 454E2-iPS-derived RPE cells. While HLA-A antigen and HLA-B antigen (Class-I) had the same alleles as HLA-A of TLHD-2, other haplotypes were completely different, and all were different in TLHD-1 (Table 3).

TABLE 3

| CD4+ cell | iPS-RPE | Class II match | Class I match | IFN-γ |
|---|---|---|---|---|
| TLHD-1 | 454E2 | mismatch | mismatch | up |
| TLHD-2 | 454E2 | mismatch | A allele match | up |

Example 2

Figure 2:
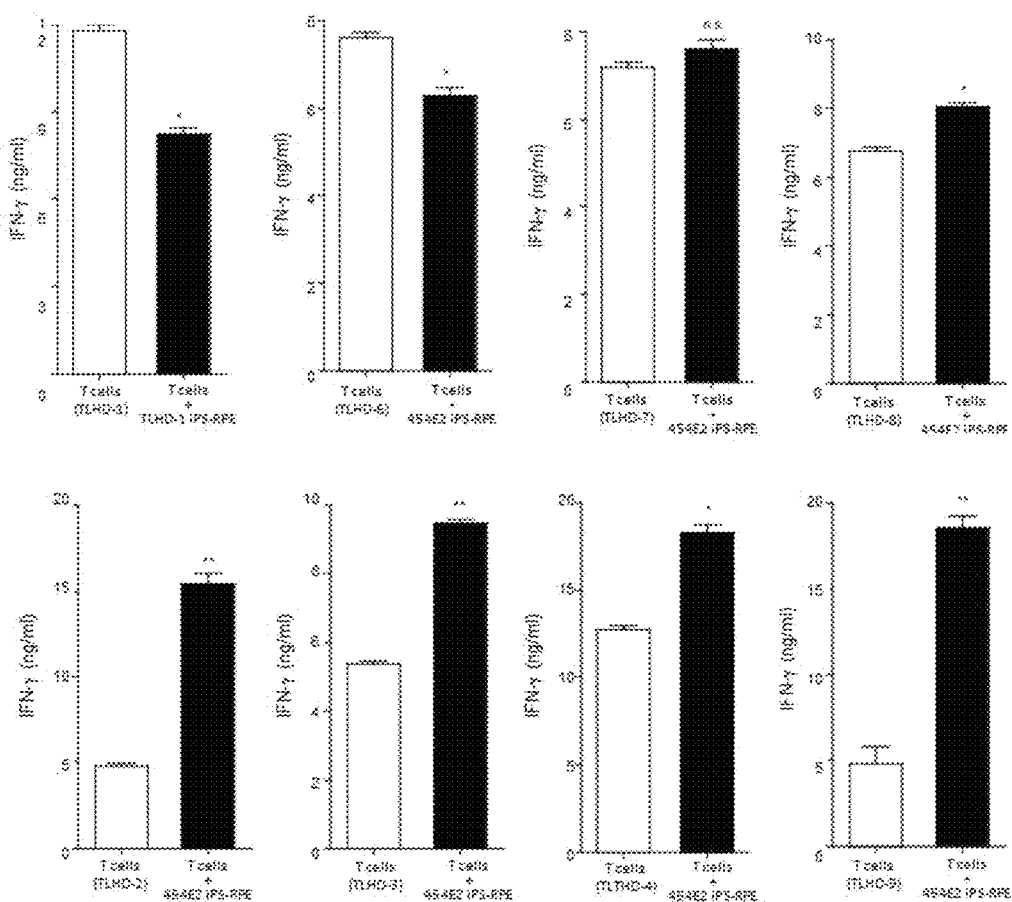
FIG. 2 shows the concentration of IFN-γ in a culture supernatant when CD4 positive T cell suspension (TLHD-2, TLHD-3, TLHD-4, TLHD-6, TLHD-7, TLHD-8, TLHD-9) and 454E2-iPS-derived RPE cells were cocultured, and when TLHD-1-derived T cell suspension and RPE cells derived from iPS cell derived from TLHD-1 were cocultured.

By a method similar to that in Example 1 except that CD4 positive T cell suspension (test subject names: TLHD-2, TLHD-3, TLHD-4, TLHD-6, TLHD-7, TLHD-8, TLHD-9) obtained in Preparation Example 2 was used as T cell suspension, and 454E2-iPS-derived RPE cells obtained in Preparation Example 1 were used at a concentration of 1×10⁴/well, the production amount of IFN-γ was measured. In addition, using TLHD-1-derived cells instead of T cell suspension and iPS cell-derived RPE cells and by a method similar to that in Example 1, the production amount of IFN-γ was measured. The results are shown in FIG. 2.

As a result, the production of IFN-γ was suppressed as compared to control in a combination of T cell suspension of TLHD-1 and iPS cell-derived RPE cells of TLHD-1, and a combination of T cell suspension of TLHD-6 and 454E2-iPS-derived RPE cells.

Therefore, autologous transplantation, or transplantation of 454E2-iPS-derived RPE cells to the test subject TLHD-6 can be judged to have a low possibility of causing a rejection response. That is, the 454E2-iPS-derived RPE cells can be used as a therapeutic agent for an ophthalmic disease of the test subject TLHD-6 or a patient having the same HLA haplotype as test subject TLHD-6, and the same alleles as test subject TLHD-6.

On the other hand, in the combinations other than of the above, the production amount of IFN-γ increased as compared to the control. Therefore, transplantation of 454E2-iPS cell-derived RPE cells to patients other than a patient with an ophthalmic disease and having the same HLA haplotype as TLHD-6 and the same alleles as TLHD-6 can be judged to have a high possibility of causing a rejection response. In this case, either 454E2-iPS cell-derived RPE cells are not utilized for the transplantation or transplantation with combined use of an immunosuppressant needs to be considered.

In TLHD-6 that showed suppressed cytokine production, alleles were the same at HLA-DR and HLA-B of 454E2-iPS cell-derived RPE cells. On the other hand, in TLHD-7 that showed high cytokine production, alleles were the same at HLA-A but different at HLA-DR. In TLHD-8, alleles were different from 454E2-iPS cell-derived RPE cells. Other cells that showed high cytokine production were different in haplotype from 454E2-iPS cell-derived RPE cells (Table 4).

TABLE 4

| CD4+ cell | iPS-RPE | Class II match | Class I match | IFN-γ |
|---|---|---|---|---|
| TLHD-1 | TLHD-1 | All match | All match | down |
| TLHD-6 | 454E2 | DR allele match | B allele match | down |
| TLHD-7 | 454E2 | DR haplotype match | A allele match | up |
| TLHD-8 | 454E2 | DR haplotype match | mismatch | up |
| TLHD-2 | 454E2 | mismatch | A allele match | up |
| TLHD-3 | 454E2 | mismatch | mismatch | up |
| TLHD-4 | 454E2 | mismatch | mismatch | up |
| TLHD-9 | 454E2 | mismatch | A allele match | up |

Example 3

Figure 3:
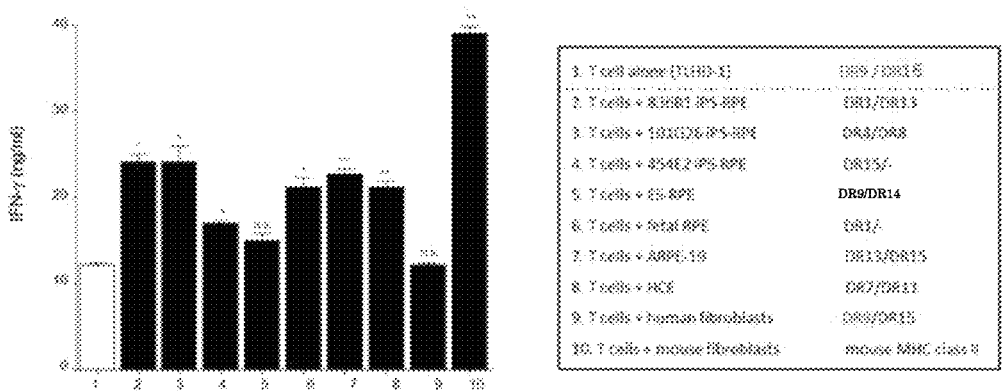
FIG. 3 shows the concentration of IFN-γ in a culture supernatant when CD4 positive T cell suspension (TLHD-1) and various RPE cells (No. 1-3, 6-10 in Table 2) or mouse fibroblast were cocultured.

By a method similar to that in Example 1 except that CD4 positive T cell suspension (TLHD-1) obtained in Preparation Example 2 was used as T cell suspension, and Nos. 1-3, 6-10 shown in Table 2 and mouse fibroblast were used at a concentration of 1×10⁴/well instead of 454E2-iPS-derived RPE so cells obtained in Preparation Example 1, the production amount of IFN-γ was measured. The results are shown in FIG. 3.

As a result, in all cells other than human fibroblast, the production amount of IFN-γ increased. Therefore, transplantation of 454E2-iPS cell-derived RPE cells to patients other than a patient with an ophthalmic disease and having the same HLA haplotype as the above-mentioned human fibroblast and the same alleles as the above-mentioned human fibroblast can be judged to have a high possibility of causing a rejection response. In this case, either 454E2-iPS cell-derived RPE cells are not utilized for the transplantation or transplantation with combined use of an immunosuppressant can be considered.

Relative to HLA-DR antigen of ES-derived RPE cells and human fibroblast, TLHD-1 had the same alleles, and others were different in haplotype (Table 5).

TABLE 5

| Lane | CD4+ cell | Cell | Class II match | IFN-γ |
|---|---|---|---|---|
| 2 | TLHD-1 | 836B1 iPS-RPE | mismatch | up |
| 3 | TLHD-1 | 101G26 iPS-RPE | mismatch | up |
| 4 | TLHD-1 | 454E2 iPS-RPE | mismatch | up |
| 5 | TLHD-1 | ES-RPE | DR allele match | up |
| 6 | TLHD-1 | fetal RPE | mismatch | up |
| 7 | TLHD-1 | ARPE-19 | mismatch | up |
| 8 | TLHD-1 | HCE | mismatch | up |
| 9 | TLHD-1 | human fibroblast | DR allele match | same |
| 10 | TLHD-1 | mouse fibroblast | mismatch | up |

Example 4

Figure 4:
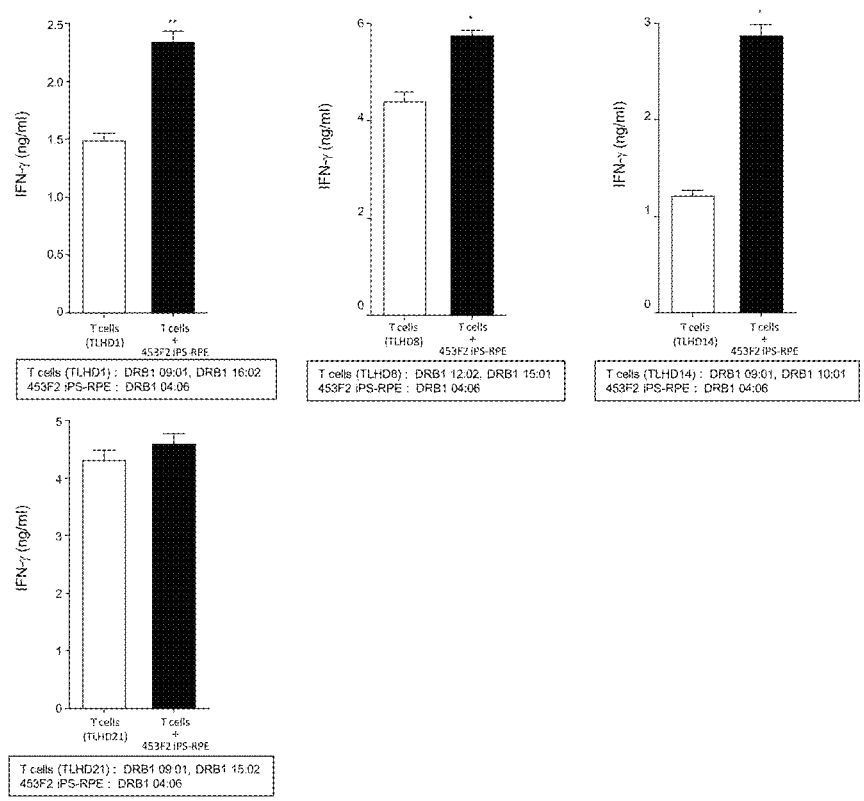
FIG. 4 shows the concentration of IFN-γ in a culture supernatant when CD4 positive T cell suspension (TLHD-1, TLHD-8, TLHD-14, TLHD-21) and 453F2-iPS-derived RPE cells were cocultured.

A similar experiment was performed except that CD4 positive T cell suspension (test subject names: TLHD-1, TLHD-8, TLHD-14, TLHD-21) obtained in Preparation Example 2 was used as T cell suspension, and 453F2-iPS-derived RPE cells shown in Table 2 were used instead of 454E2-iPS-derived RPE cells obtained in Preparation Example 1. The results are shown in FIG. 4.

Figure 5:
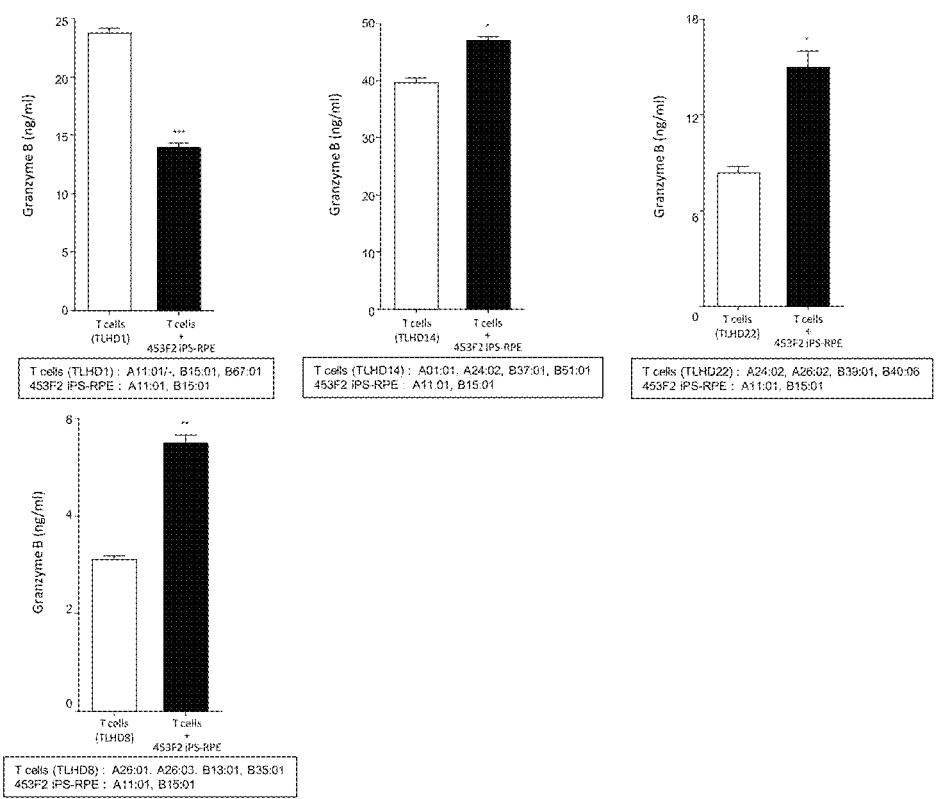
FIG. 5 shows the concentration of Granzyme B in a culture supernatant when CD8 positive T cell suspension (TLHD-1, TLHD-8, TLHD-14, TLHD-22) and 453F2-iPS-derived RPE cells were cocultured.

Alternatively, a similar experiment was performed except that CD8 positive T cell suspension (test subject names: TLHD-1, TLHD-8, TLHD-14, TLHD-22) obtained in Preparation Example 2 was used as T cell suspension in Example 1, and 453F2-iPS-derived RPE cells shown in Table 2 were used instead of 454E2-iPS-derived RPE cells obtained in Preparation Example 1. The results are shown in FIG. 5.

As a result, the production of Granzyme B was suppressed as compared to control in a combination of CD8 positive T cell suspension of TLHD-1 and 453F2-iPS-derived RPE cells. Therefore, transplantation of 453F2-iPS-derived RPE cells to the test subject TLHD-1 can be judged to have a low possibility of causing a rejection response. That is, the 453F2-iPS-derived RPE cells can be used as a therapeutic agent for an ophthalmic disease of test subject TLHD-1 or a patient having the same HLA haplotype as the test subject TLHD-1, and the same alleles as the test subject TLHD-1.

Example 5

Figure 6:
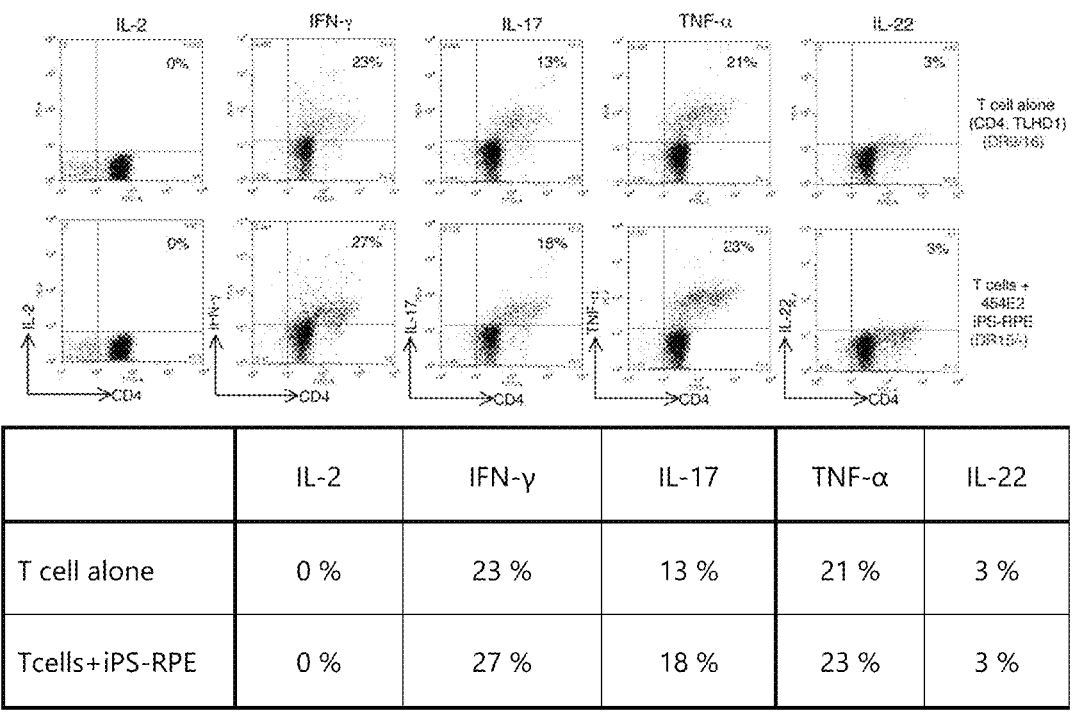
FIG. 6 shows the ratio of CD4 positive T cells that produced IL-2, IFN-γ, IL-17, TNF-α, IL-22 by FACS when CD4 positive T cell suspension (TLHD-1) and 454E2-iPS-derived RPE cells were cocultured.

In a 96 well plate, an anti-CD3 antibody was added at 1 µg/ml to CD4 positive T cell suspension (TLHD-1) obtained in Preparation Example 2 and dispensed to the well at a concentration of $5\times10^5$ cells/well. 454E2-iPS-derived RPE cells homozygous at 3 gene loci of HLA obtained in Preparation Example 1 were added to each well at a concentration of $1\times10^4$/well, and cultured, wherein the suspension without addition was used as a control. After culture for 48 hr, the cells were recovered, and the production of IL-2, IFN-γ, IL-17, TNF-α, IL-22 in CD4 positive T cells were respectively measured by FACS. The results are shown in FIG. 6.

As a result, it was found that IFN-γ, IL-17 and TNF-α can be utilized as an index of cytokine production in anti-CD4 positive T cells.

Figure 7A:
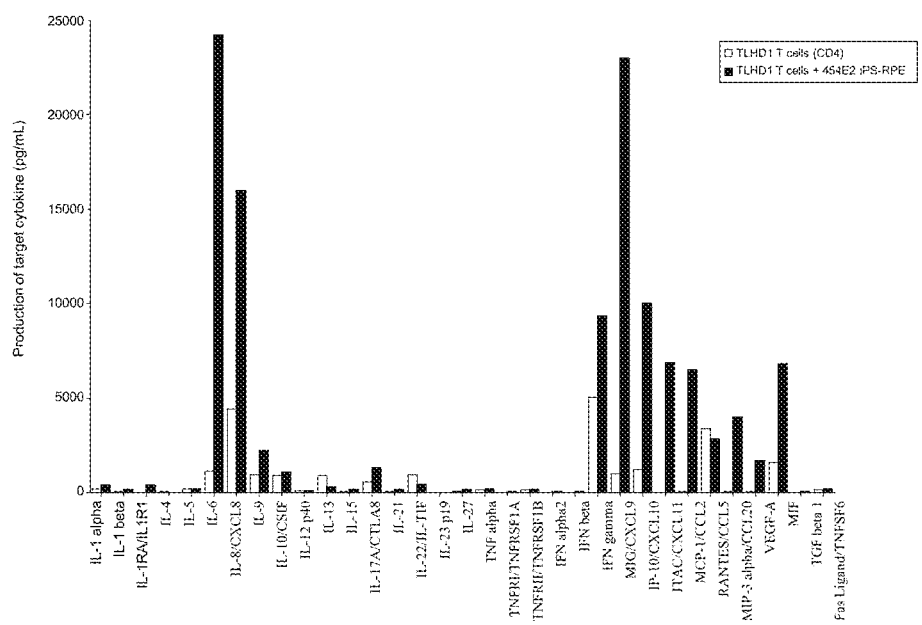
FIG. 7 shows the production amount of various cytokines when CD4 positive T cell suspension (TLHD-1, TLHD-10) and 454E2-iPS-derived RPE cells were cocultured.
Figure 7B:
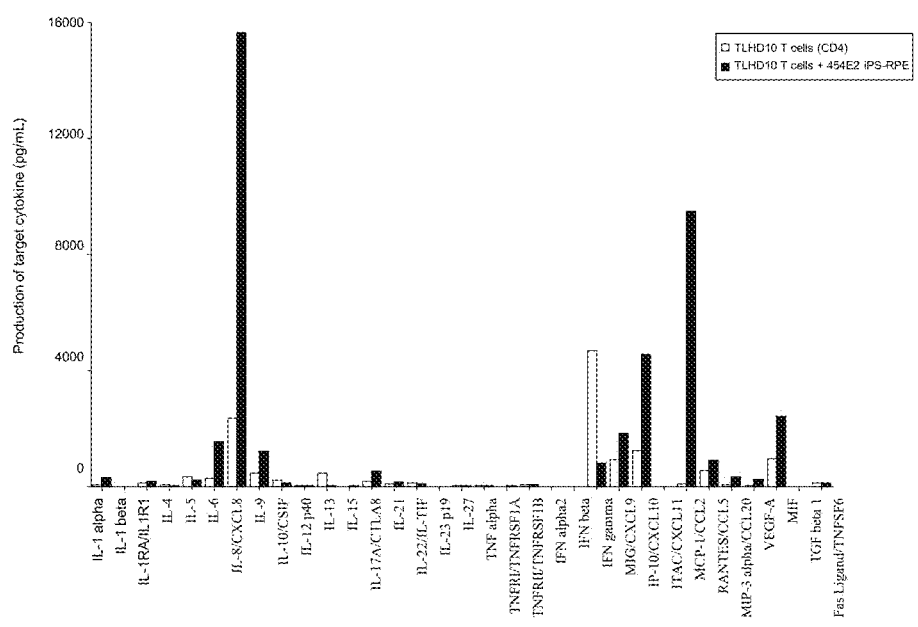

In addition, a similar experiment was further performed using the CD4 positive T cell suspensions (TLHD-1 and TLHD-10) obtained in Preparation Example 2, and various cytokine production amounts were compared (FIGS. 7a and b).

As a result, among many cytokines, the expression level of IFN-γ alone decreased when 454E2-iPS cell-derived RPE cells (homozygous at 3 gene loci of HLA-A, HLA-B, HLA-DR) were used for T cells (alleles of all genotypes of 3 gene loci of HLA-A, HLA-B, HLA-DR are same) of the test subject name TLHD-10. Thus, it was found that IFN-γ is suitable as an index of whether or not a rejection response occurs.

Example 6

Figure 8:
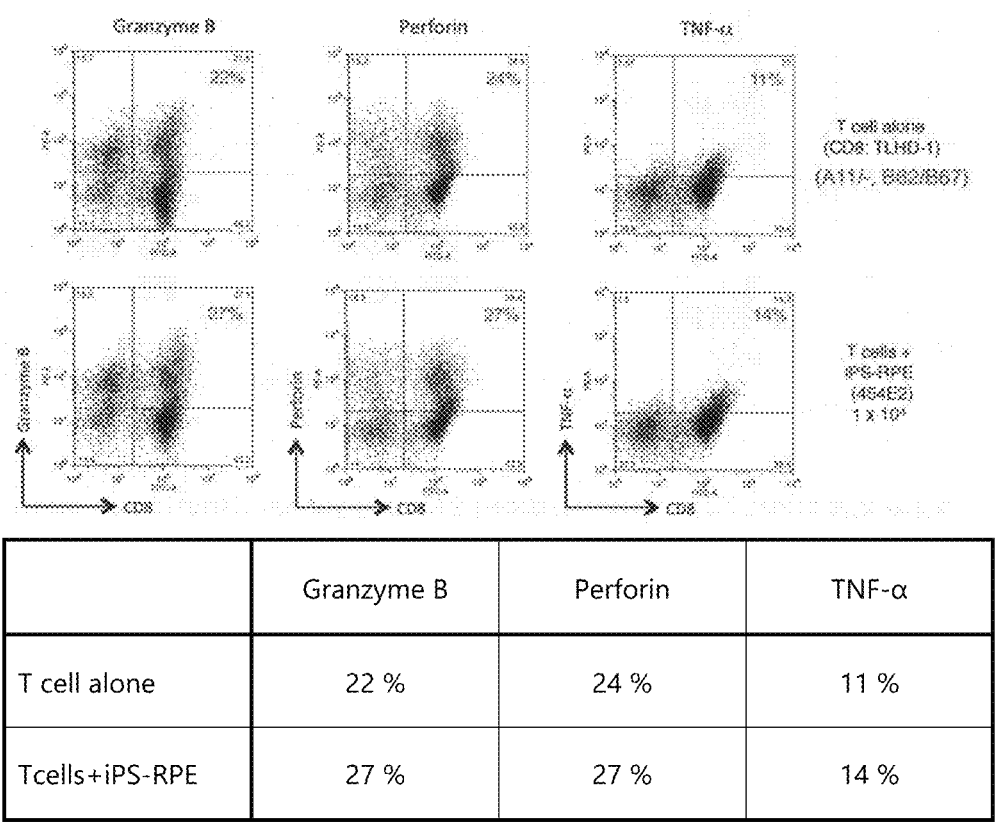
FIG. 8 shows the ratio of CD8 positive T cells that produced Granzyme B, Perforin and TNF-α by FACS when CD8 positive T cell suspension (TLHD-1) and 454E2-iPS-derived RPE cells were cocultured.

In a 96 well plate, an anti-CD8 antibody was added at 1 µg/ml to CD8 positive T cell suspensions (TLHD-1) obtained in Preparation Example 2 and dispensed to the well at a concentration of $1\times10^5$ cells/well. 454E2-iPS-derived RPE cells obtained in Preparation Example 1 were added to each well at a concentrations of $1\times10^4$/well, and cultured, wherein the suspension without addition was used as a control. After culture for 48 hr, the cells were recovered, and the production of Granzyme B, Perforin, TNF-α in the CD8 positive T cells was each measured by ELISA. The ratio of double positive cells is shown in FIG. 8.

As a result, it was suggested that a cytotoxic substance produced by CD8 positive T cells can be used for screening for a rejection response.

Example 7

Figure 9:
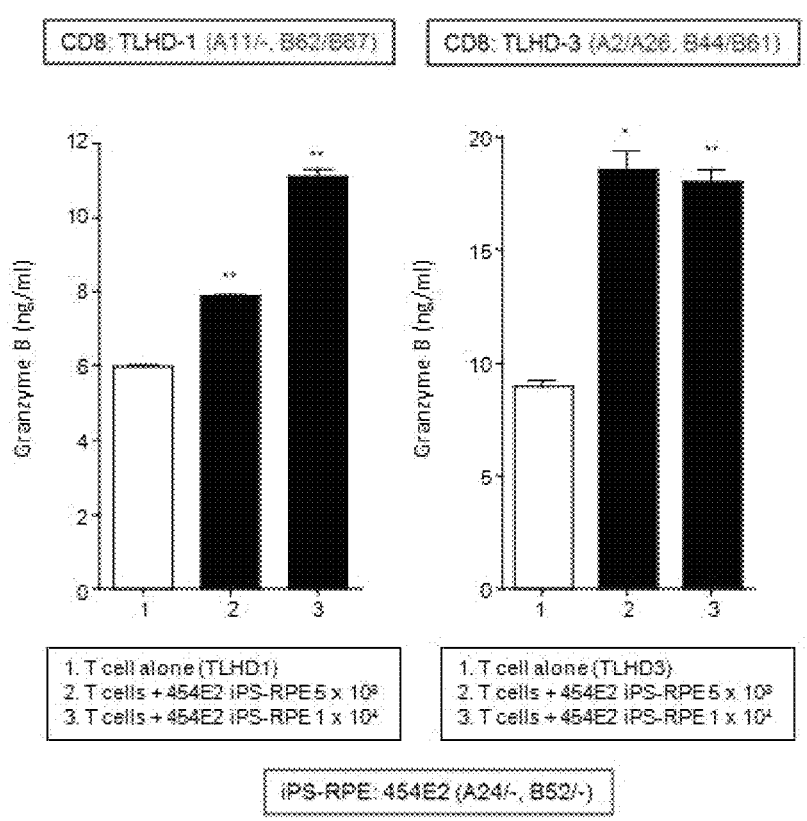
FIG. 9 shows the concentration of Granzyme B in a culture supernatant when CD8 positive T cell suspension (TLHD-1, TLHD-3) and 454E2-iPS-derived RPE cells were cocultured.

A method similar to that in Example 1 was performed except that suspensions of CD8 positive T cells (test subject names: TLHD-1, TLHD-3) were used instead of CD4 positive T cells and production of Granzyme B was measured instead of IFN-γ. The results are shown in FIG. 9.

As a result, both TLHD-1 and TLHD-3 showed an increased production of Granzyme B at all 2 kinds of concentrations as compared to the control. Therefore, transplantation of 454E2-iPS-derived RPE cells to test subjects TLHD-1 and TLHD-3 can be judged to have a high possibility of causing a rejection response.

HLA antigens of TLHD-1 and TLHD-3 showed different haplotype from that of both HLA-A antigen and HLA-B antigen of 454E2-iPS-derived RPE cells (Table 6).

TABLE 6

| CD8+Tcell | iPS-RPE | Class I match | Class II match | Granzyme B |
|---|---|---|---|---|
| TLHD-1 | 454E2 | mismatch | mismatch | up |
| TLHD-3 | 454E2 | mismatch | mismatch | up |

Example 8

Figure 10:
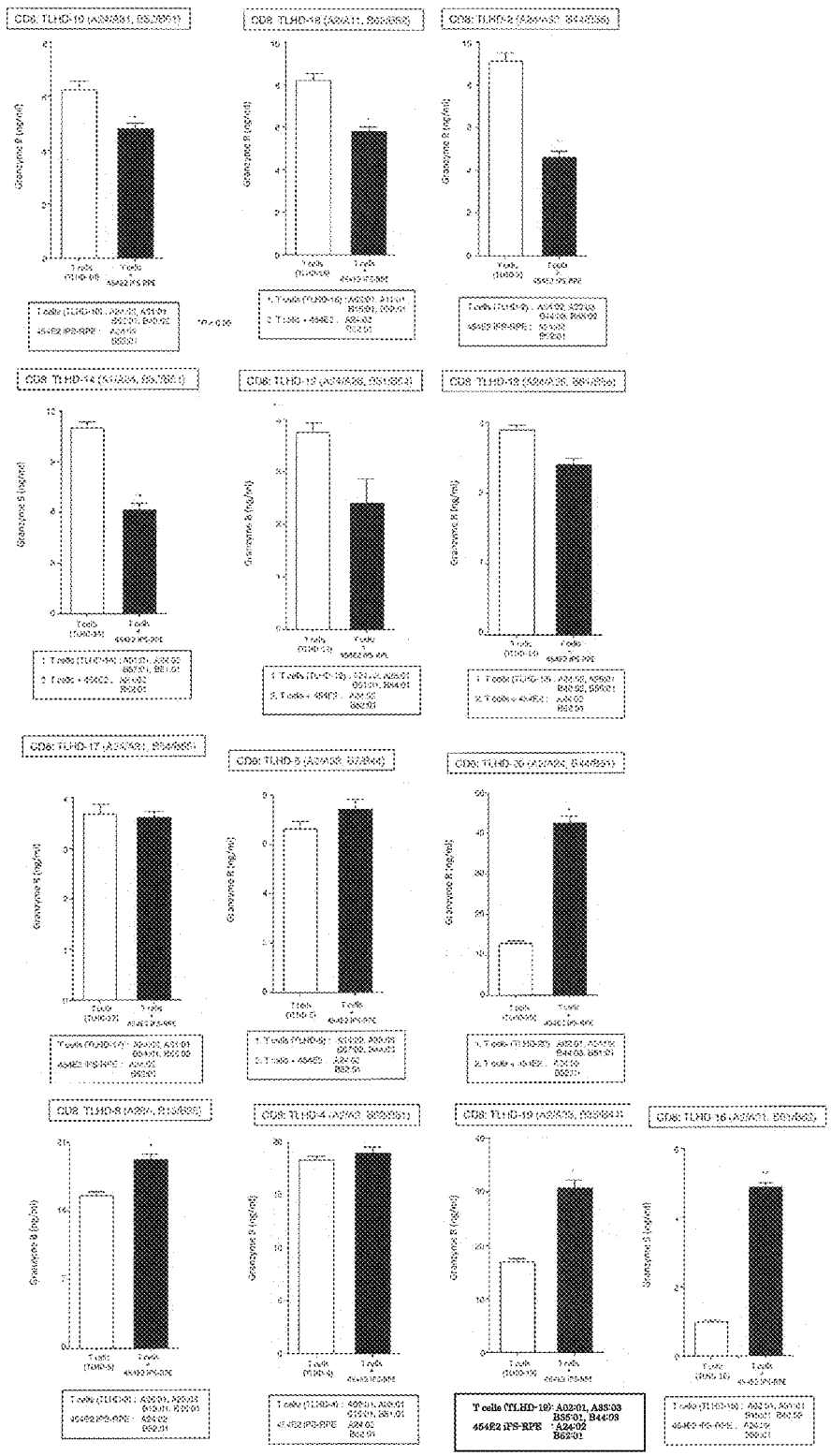
FIG. 10 shows the concentration of Granzyme B in a culture supernatant when CD8 positive T cell suspension (TLHD-2, 4, 5, 8, 10, 12, 13, 14, 16, 17, 18, 19, 20) and 454E2-iPS-derived RPE cells were cocultured.

A method similar to that in Example 1 was performed except that suspensions of CD8 positive T cells (test subject names: TLHD-2, 4, 5, 8, 10, 12, 13, 14, 16, 17, 18, 19, 20) were used instead of CD4 positive T cells and production of Granzyme B was measured instead of IFN-γ. The results are shown in FIG. 10.

As a result, the production of Granzyme B was suppressed as compared to control in a combination of T cell suspensions of TLHD-10, TLHD-18, TLHD-2, TLHD-14, TLHD-12, TLHD-13, TLHD-17 and 454E2-iPS-derived RPE cells. Therefore, transplantation of 454E2-iPS-derived RPE cells to the test subjects TLHD-10, TLHD-18 can be judged to have a low possibility of causing a rejection response. While TLHD-2, TLHD-14, TLHD-12, TLHD-13, TLHD-17 matched only with the alleles of HLA-A, the possibility of not causing a rejection response needs to be considered.

On the other hand, in the combinations other than of the above, the production amount of Granzyme B increased as compared to the control. Therefore, transplantation of 454E2-iPS cell-derived RPE cells to the corresponding test subjects can be judged to have a high possibility of causing a rejection response. In this case, either 454E2-iPS cell-derived RPE cells are not utilized for the transplantation or transplantation with combined use of an immunosuppressant can be considered.

In TLHD-10 and TLHD-18 that showed suppressed production of Granzyme B, both the haplotypes and alleles matched in HLA-A or HLA-B, and HLA-DR. On the other hand, in TLHD-2, TLHD-14, TLHD-12, TLHD-13, haplotype and alleles were the same at HLA-A or HLA-B of 454E2-iPS cell-derived RPE cells. On the other hand, also in TLHD-5 and TLHD-20 that showed increased production of Granzyme B, haplotype and alleles were the same at HLA-A or HLA-B of 454E2-iPS cell-derived RPE cells, and in TLHD-8, only HLA-DR haplotype was the same (Table 7).

Thus, even when allele and haplotype partially match, production of Granzyme B may increase. However, when at least one of the alleles of HLA-A, HLA-B or and HLA-DR is the same, it can be judged that the possibility of causing a rejection response is low. Furthermore, when at least any two of the alleles of HLA-A, HLA-B or HLA-DR are the same, it can be judged that the possibility of causing a rejection response is lower, and when all alleles of HLA-A, HLA-B and HLA-DR are the same, it can be judged that the cells are suitable for transplantation. On the contrary case, either the cells are not utilized for the transplantation or the case can be used as an index for consideration of transplantation with combined use of an immunosuppressant. Other cells that showed high granzyme B production were different in haplotype from 454E2-iPS cell-derived RPE cells.

TABLE 7

| CD8+Tcell | iPS-RPE | Class I match | Class II match | Granzyme B |
|---|---|---|---|---|
| TLHD-10 | 454E2 | A allele match, B allele match | DR allele match | down |
| TLHD-18 | 454E2 | B allele match | DR allele match | down |
| TLHD-2 | 454E2 | A allele match | mismatch | down |
| TLHD-14 | 454E2 | A allele match | mismatch | down |
| TLHD-12 | 454E2 | A allele match | mismatch | down |
| TLHD-13 | 454E2 | A allele match | mismatch | down |
| TLHD-17 | 454E2 | A allele match | mismatch | down |
| TLHD-5 | 454E2 | A allele match | mismatch | up |
| TLHD-20 | 454E2 | A allele match | mismatch | up |
| TLHD-8 | 454E2 | mismatch | DR haplotype match | up |
| TLHD-4 | 454E2 | mismatch | mismatch | up |
| TLHD-19 | 454E2 | mismatch | DR allele match | up |
| TLHD-16 | 454E2 | mismatch | mismatch | up |

Example 9

(Prediction Test)

In a 96 well plate, an anti-CD3 antibody is added at 1 μg/ml to CD4 positive T cell suspension (monkey disease model C) obtained in Preparation Example 4 and the suspension was dispensed to the well at a concentration of $5 \times 10^5$ cells/well. Normal monkey B-iPS-derived RPE cells or disease model monkey C-iPS-derived RPE cells obtained in Preparation Example 3 are added to each well at $1 \times 10^4$/well, and cultured, wherein the suspension without addition was used as a control. After culture for 48 hr, the culture supernatant is recovered, and the concentration of IFN-γ in the culture supernatant is measured by ELISA.

A method similar to the aforementioned method is performed except that a suspension of CD8 positive T cells (monkey disease model C) is used instead of CD4 positive T cells and production of Granzyme B is measured instead of IFN-γ.

In the case of normal monkey B-iPS-derived RPE cells, the production amounts of both IFN-γ and Granzyme B increase as compared to the control, whereas in the case of disease model monkey C-iPS-derived RPE cells, the production amounts of both IFN-γ and Granzyme B are suppressed as compared to the control.

(Transplantation Test)

Normal monkey B-iPS-derived RPE cells or disease model monkey C-iPS-derived RPE cells are transplanted to one eye of disease model monkey C, according to the method described in Invest Ophthalmol Vis Sci. 1995 February; 36(2):381-90. On day 28 after transplantation, a section of fundus is imaged like a tissue section by using fundus photograph and OCT (Optical coherence tomograph), and the condition of the retina is confirmed.

Allogeneic transplantation of normal monkey B-iPS-derived RPE cells shows clear rejection responses such as fibrotic change of graft periphery, leakage of fluorescence by fluorescein fundus angiography, and high-intensity lesion under retina in OCT. Allogeneic transplantation of disease model monkey C-iPS-derived RPE cells does not show such clear rejection response, leakage of fluorescence by fluorescein fundus angiography is absent, graft is engrafted, and disorders such as thinning of sensory retina and the like do not occur.

Example 10

(Prediction Test)

A method similar to that in Example 8 is performed except that normal monkey A-iPS-derived RPE cells (homozygous at 3 gene loci of MHC) obtained in Preparation Example 3 or disease model monkey C-iPS-derived RPE cells are used at a concentration of $1 \times 10^4$/well, and the production amount of IFN-γ is measured.

A method similar to the aforementioned method is performed except that a suspension of CD8 positive T cells (monkey disease model C) is used instead of CD4 positive T cells and production of Granzyme B is measured instead of IFN-γ.

In both normal monkey A-iPS-derived RPE cells and disease model monkey C-iPS-derived RPE cells, the production amounts of both IFN-γ and Granzyme B are suppressed as compared to the control.

(Transplantation Test)

A method similar to the transplantation test in Example 8 is performed except that normal monkey A-iPS-derived RPE cells (homozygous at 3 gene loci) or disease model monkey C-iPS-derived RPE cells are used as iPS-derived RPE cells, iPS-derived RPE cells are transplanted to one eye of disease model monkey C. On day 28 after transplantation, a section of fundus is imaged like a tissue section by using fundus photograph and OCT (Optical coherence tomograph), and the condition of the retina is confirmed.

Allogeneic transplantation of normal monkey A-iPS-derived RPE cells (homozygous at 3 gene loci) shows no clear rejection response, like autologous transplantation of disease model monkey C-iPS-derived RPE cells, leakage of fluorescence by fluorescein fundus angiography is absent, graft is engrafted, and disorders such as thinning of sensory retina and the like do not occur.

INDUSTRIAL APPLICABILITY

According to the present invention, however, when the genotype of 3 gene loci of HLA-A, HLA-B and HLA-DR on the donor side is homozygous in RPE cell transplantation, rejection can be suppressed by merely matching one of the HLA loci of the recipient. Since immunologically incompatible cells for so transplantation can be distinguished and selected by previously collecting blood samples, the burden on patients can be reduced by avoiding incompatible cells for transplantation. The cells selected by this method can be used for RPE cell transplantation. In addition, the present invention used to determine whether an immunosuppressant is necessary can contribute to the selection of a treatment plan. Thus, the present invention contributes to marked improvement of treatment efficiency by allogeneic transplantation, and also affords effects such as reduction of the preparation costs of cells unsuitable for transplantation and the like.

This application is based on patent application No. 2014-032325 filed in Japan (filing date: Feb. 21, 2014), the contents of which are incorporated in full herein.

The invention claimed is:

1. A method of producing an allogeneic retinal pigment epithelial (RPE) cell as an active ingredient of a therapeutic agent for a patient with an ophthalmic disease, comprising:

(i) a step of examining genotypes of alleles of an HLA-A gene locus, an HLA-B gene locus, and an HLA-DR gene locus of patient-derived T cells;

(ii) a step of producing the RPE by obtaining RPE directly from an eye, by isolating RPE from an eye and growing it in a culture medium, by differentiating a stem cell into the RPE, or by differentiating a progenitor cell into the RPE, wherein the produced RPE is allogeneic, has an allele matching the allele at each gene locus examined in step (i), and does not have the same HLA haplotype as the patient-derived T cells.

2. The method according to claim 1, wherein the retinal pigment epithelial cell in step (ii) has an HLA-A gene locus, an HLA-B gene locus and an HLA-DR gene locus, and a genotype of each locus is homozygous.

\* \* \* \* \*